United States Patent [19]

Primrose et al.

[11] Patent Number: 5,691,173
[45] Date of Patent: Nov. 25, 1997

[54] FERMENTATION PROCESS FOR PREPARATION OF COMPACTIN

[75] Inventors: Scott Primrose; David King; Ed Yaworski; Jayaramaiyer Radhakrishnan; David He; Xinfa Xiao, all of Winnipeg, Canada

[73] Assignee: Apotex, Inc., Ontario, Canada

[21] Appl. No.: 715,771

[22] Filed: Sep. 19, 1996

[30] Foreign Application Priority Data

Sep. 21, 1995 [NZ] New Zealand ............................ 280074

[51] Int. Cl.$^6$ ...................................................... C12P 17/06
[52] U.S. Cl. .......................... 435/125; 435/256.3; 435/933
[58] Field of Search ....................... 435/125, 933, 435/256.3

[56] References Cited

U.S. PATENT DOCUMENTS

| 3,983,140 | 9/1976 | Endo et al. | 435/72 |
| 4,049,495 | 9/1977 | Endo et al. | 435/125 |

Primary Examiner—Herbert J. Lilling
Attorney, Agent, or Firm—Nixon & Vanderhye P. C.

[57] ABSTRACT

A novel microorganism, *Penicillium adametzioides* and a process of using the microorganism to produce compactin, the process consisting of fermentation in a nutrient medium.

5 Claims, No Drawings

FERMENTATION PROCESS FOR PREPARATION OF COMPACTIN

FIELD OF THE INVENTION

The present invention relates to a new fermentation process for production of compactin (I) by cultivation of compactin-producing microorganism *Penicillium adametzioides* G. Smith.

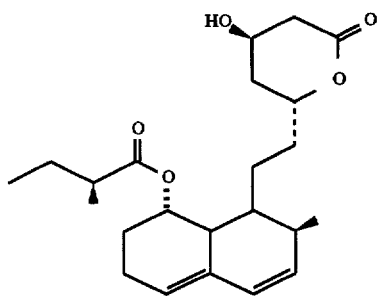

(I)

BACKGROUND ART

Several patents have been issued which involved fermentative production of compactin by cultivation of particular microorganisms.

U.S. Pat. Nos. 3,983,140 (Sep. 28, 1976) and 4,049,495 (Sep. 20, 1977) patented by A. Endo et al claimed fermentative production of compactin by cultivation of compactin-producing microorganism *Penicillium citrinum*.

SUMMARY OF THE INVENTION

An object of this invention is to provide a new process for producing physiologically active substance compactin which comprises cultivating *Penicillium adametzioides* G. Smith and then recovering said substance from a cultured broth. The above strain is a natural strain collected in China and has been identified as an undescribed compactin-producing species.

In the present application a process for the production of compactin having the structure (I) which comprises cultivating compactin-producing microorganism *penicillium adametzioides* G. Smith, in a nutrient medium and recovering compactin from the cultured broth.

Based upon taxonomic studies, this Penicillium, isolated and identified as an undescribed microorganism has been designated AFI-624 in the culture collection of Apotex Fermentation Inc. and a culture thereof has been placed on permanent deposit, under the terms of the Budapest Treaty, with the American Type Culture Collection (ATCC) 12301 Parklawn Drive, Rockville, MD 20852, USA, on Jan. 30, 1997 and has been assigned accession number ATCC Collection (ATCC) 74399. This isolate belongs in *Penicillium adametzioides* and that species belongs in subgenus Aspergilloides, section Implicata (samples of which have also been deposited at the University of Alberta, Microfungus Collection and Herbarium (UAMH) under accession No. UAMH #7634).

The culture was inoculated on Potato-Dextrose-Agar slant or CM-1 agar slant, incubated at 23°–28°±2° C. until mature, then transplanted into flasks containing different media and shaken at a temperature of 23° C. to 28° C.±2° and pH of 5 to 9. Production levels of compactin on day 7 to day 11 ranged from hundreds of mg/l to 1.6 g/l. In the fermentation media, we used nutrients such as glucose, cornstarch, lactose, glycerol, $(NH_4)_2SO_4$, $NaNO_3$, amicase, peptone, soybean flour, meat extract, various yeast extracts, soy protein, cornmeal, malt extract, peptonized milk, oatmeal, tomato paste, corn steam liquor etc. and other materials such as $MgSO_4.7H_2O$, NaCl, $KH_2PO_4$ KCl, $MnSO_4.H_2O$, $CaCO_3$, $KNO_3$, $K_2HPO_4$, $CoCl_2$, $FeSO_4$, $CuCl_2$, $CaCl_2$, $H_3BO_3$, $(NH_4)_6Mo_7.H_2O$, $ZnSO_4$, etc.

This invention has been scaled up to 20-L, 1,500-L and 14,000-L fermentor and found to produce more than 800 mg of compactin per litre of broth.

Several media we used are listed below:

| CM-1 agar: | |
|---|---|
| Starch | 1.00% |
| $MgSO_4$ | 0.05% |
| NaCl | 0.05% |
| $KNO_3$ | 0.30% |
| $K_2HPO_4$ | 0.03% |
| $CaCO_3$ | 0.10% |
| Agar | 2.00% |
| pH | natural |

| 624-PM: | |
|---|---|
| Lactose | 7.0% |
| Corn meal | 2.0% |
| Soybean meal | 8.5% |
| Yeast extract | 0.5% |
| Corn steam liquor | 0.2% |
| Starch | 0.3% |
| KCl | 0.06% |
| $KH_2PO_4$ | 0.04% |
| $MgSO_4$ | 0.0003% |
| P2000 | 0.0008% |
| pH | natural |

| M3-5: | |
|---|---|
| Glucose | 12% |
| Peptone | 2% |
| Amicase | 4% |
| $(NH_4)_2SO_4$ | 0.8% |
| $MgSO_4.7H_2O$ | 0.05% |
| P2000 | 0.1% |
| pH | 5.5 |

| Y-5: | |
|---|---|
| Lactose | 6% |
| Ardamine pH | 1% |
| Soy protein | 0.2% |
| Betaine | 0.06% |
| KCl | 0.2% |
| $KH_2PO_4$ | 0.08% |
| $MnSO_4.H_2O$ | 0.003% |
| P2000 | 0.1% |
| pH | 6.8 |

| CMP-12: | |
|---|---|
| Glucose | 12% |
| Corn starch | 1% |
| Soybean flour | 2% |
| Meat extract | 0.5% |
| Peptone | 0.5% |
| NaCl | 0.2% |
| $KH_2PO_4$ | 0.05% |
| $MgSO_4.7H_2O$ | 0.05% |
| P2000 | 0.1% |
| pH | 5.8 |

| MPG: | |
|---|---|
| Malt extract | 3% |
| Peptone | 1% |
| Glucose | 2% |
| pH | natural |

| BM: | |
|---|---|
| Glucose | 5% |
| Beer yeast | 2% |
| Tomato paste | 3% |
| Oat meal | 2% |

-continued

| | |
|---|---|
| Sodium acetate | 1% |
| (NH$_4$)$_2$SO$_4$ | 0.5% |
| KH$_2$PO$_4$ | 0.2% |
| Trace elements solution | 1 mL |
| pH | 7 |
| GPY: | |
| Glucose | 4.5% |
| Peptonized milk | 2.4% |
| Yeast extract | 0.25% |
| P2000 | 0.25% |
| pH | 7.4 |
| LM: | |
| Dextrose | 2% |
| Glycerol | 2% |
| Ardamine pH | 1% |
| Malt extract | 2% |
| CoCl$_2$.6H$_2$O | 8 mg/L |
| P2000 | 0.25% |
| pH | 7 |

After cultivation, compactin may be isolated and recovered from a culture broth by a suitable combination of conventional techniques such as filtration, solvent extraction, vacuum distillation and crystallization.

This invention will be illustrated by the following examples. Various modifications may be made by those skilled in the art for cultivation and recovery of compactin.

Although this invention is explained hereinbelow principally with respect to the specific strain, it is well-known in the art that various properties of all microorganisms belonging to the genus Penicillium are note definite, but the microorganisms of the genus Penicillium may be easily varied naturally and artificially. It is, accordingly, to be noted that all strains which are of the genus Penicillium and capable of producing compound I including varieties and mutants, are contemplated and usable in this invention.

EXAMPLE 1

AFI-624 culture was inoculated on CM-1 agar slant and incubated at 28° C. The mature slant culture was inoculated into 250-ml shake flask containing 50 ml of 624-SM seed medium and incubated at 250 rpm and 27° C. for 2 days. The 2-day seed culture was inoculated into 250-ml shake flask containing 50 ml of 624-PM production medium at an inoculum size of approx. 4 to 7% v/v and incubated at 23° to 28° C. and 200 to 250 rpm. The fermentation broth was harvested on day 7, 9 and 11. The compactin titer of the broth was determined by HPLC.

AFI-624 COMPACTIN PRODUCTION RESULTS FOR EXAMPLE 1

| | GROWTH TEMPERTURE (°C.) | | |
|---|---|---|---|
| HARVEST DAY | 23.00 | 26 | 28 |
| Day 7 | 1275 | 1015 | 825 |
| Day 9 | 1330 | 1220 | 860 |
| Day 11 | 1090 | 1410 | 1085 |

*Titers in table are total compactin in mg/L based on duplicate shake flasks.

Fermentation broth was acidified to pH 3.0 using 10% sulphuric acid under agitation. The acidified broth was further agitated at 70° C. for 1 hour, and then cooled down to room temperature. The slurry was filtered through a Celite bed. The acidic cake was extracted with 3.5 volumes of toluene at reflux for 6 hours. The hot slurry was filtered and washed with 1 volume of toluene. Organic extract was concentrated to small volume and cooled down to 5° C. The precipitated solids were filtered and washed with cold toluene to give over 90% pure compactin with 75% overall yield calculated from the harvest titer in the broth. Compactin identity was confirmed by direct comparison of NMR and mass spectra with those for an authentic sample.

EXAMPLE 2

624-SM seed medium was inoculated with AFI-624 slant cultures grown on Potato dextrose agar or CM-1 medium. Seed cultures were grown at 26° C., shaking at 200 rpm for 2 days. Various types of production media were inoculated from seed culture at 3–5% v/v and incubated shaking at 200 rpm 24° C.±2° C. Production flasks were harvested on the appropriate day and samples submitted for HPLC determination of compactin concentration.

Afi-624 Compactin Production Results for Example 2
Testing of AFI-624 in Various Production Media

| Medium Tested | Slant Culture | Incubation Period (Days) | | |
|---|---|---|---|---|
| | | Day 7 | Day 9 | Day 11 |
| CMP-12 | PDA | 455 ± 48[1] | 419 ± 8 | 1245 ± 94 |
| Y-5 | PDA | 144 ± 17 | 303 ± 8 | 631 ± 48 |
| 624-PM | PDA | 840 ± 91 | 1144 ± 52 | 1365 ± 99 |
| 624-PM | CM-1 | 1228 ± 41 | 1391 ± 94 | 1337 ± 121 |
| Y-5 | CM-1 | 190 ± 22 | 304 ± 14 | 353 ± 10 |
| M3.5(12%) | CM-1 | 855 ± 56 | 1149 ± 52 | 1643 ± 69 |
| CMP-12 | CM-1 | 563 ± 10 | 689 ± 41 | 1129 ± 46 |
| GPY | CM-1 | 428 ± 16 | 540 ± 76 | 478 ± 20 |
| MPG | CM-1 | 37 ± 1 | 40 | 45 ± 3 |
| BM | CM-1 | 1237 ± 97 | 1459 ± 64 | 1463 ± 128 |
| LM | CM-1 | 171 ± 18 | 243 ± 16 | 271 ± 6 |

Note:
[1]Compactin concentrations in table are in mg\L.

EXAMPLE 3

AFI-624 culture was inoculated on PDA slants and incubated at 23° C. The mature slant culture was inoculated into 250-ml shake flask containing 50 ml of 624-SM seed medium and incubated at 250 rpm and 23° C. for 2 days. The 2-day seed culture was inoculated at 10% v/v into cultural bottle containing 1,000 ml of M3.5 medium and a stirring bar, incubated at 23° C. for 24 h, and then, transplanted at 10% inoculum to 20 L fermentor containing M3–5 medium. Six-day fermentation in this fermentor at 23° C. gave a compactin titer of 862 mg/l.

EXAMPLE 4

The same conditions as example 3 were used to get the cultural bottle culture. The culture was inoculated at 10% inoculum to 20 L fermentor containing M3.5 seed medium, grown at 23° C. for 24 h, and then transplanted at 10% inoculum to 150 L fermentor containing M3.5 medium. After 24 h continuing growth at 23° C., the culture was transplanted at 10% inoculum to 1500 L fermentor containing M3–5 production medium. Six-day fermentation in this fermentor at 23° C. gave a compactin titer of 818 mg/l.

EXAMPLE 5

The same conditions as example 4 were used to get 24-h 150 L fermentor culture. This culture was inoculated at 10% inoculum to 1500 L fermentor containing M3.5 seed medium and grown at 23° C. for 24 h. The 1500 L fermentor culture was transplanted at 10% inoculum to 14000 L fermentor containing M3-5 production medium. Seven-day fermentation in this fermentor at 23° C. gave a compactin titer of 883 mg/l.

What is claimed:

1. A process for the production of compactin having the structure (I) which comprises cultivating compactin-producing microorganism *penicillium adametzioides* G. Smith, in a nutrient medium and recovering compactin from the cultured broth.

2. A process according to claim 1, wherein the cultivation is effected at temperature ranging from 23° to 28° C.

3. A process according to claim 1, wherein the pH of said culture medium is within the range of 5 to 9.

4. A process according to claim 1, wherein the cultivation period is within the range of 4 days to 11 days.

5. A process according to claim 1, wherein in the nutrient medium, the carbon sources is glucose, the nitrogen source is peptone and the inorganic salts are ammonium sulphate and magnesium sulphate.

\* \* \* \* \*